United States Patent [19]

Schreier et al.

[11] Patent Number: 5,252,348
[45] Date of Patent: Oct. 12, 1993

[54] ARTIFICIAL VIRAL ENVELOPES

[75] Inventors: Hans Schreier, Gainesville, Fla.; Ramesh Chander, Bombay, India; Arlene A. Stecenko, Gainesville, Fla.

[73] Assignee: Univ. of Florida Research Foundation, Inc., Gainesville, Fla.

[21] Appl. No.: 923,016

[22] Filed: Jul. 30, 1992

Related U.S. Application Data

[63] Continuation of Ser. No. 600,641, Oct. 19, 1990, abandoned.

[51] Int. Cl.$^5$ .................. A61K 9/127; B01J 13/02
[52] U.S. Cl. ...................... 424/450; 264/41; 424/88; 424/89; 436/829
[58] Field of Search .................. 424/450, 88, 89; 264/4.1; 436/829

[56] References Cited

U.S. PATENT DOCUMENTS

| | | | |
|---|---|---|---|
| 4,792,331 | 12/1988 | Pillippot et al. | 604/187 |
| 4,927,637 | 5/1990 | Morano et al. | 424/450 |

FOREIGN PATENT DOCUMENTS

| | | |
|---|---|---|
| 0047480 | 3/1982 | European Pat. Off. . |
| 0298280 | 1/1989 | European Pat. Off. . |
| 0306912 | 3/1989 | European Pat. Off. . |
| 8805307 | 7/1988 | PCT Int'l Appl. . |

OTHER PUBLICATIONS

Weiner, Advanced Drug Delivery Reviews 3, 307–341 (1989).
Deamer & Uster Liposome Prep. Methods & Mechanism Chapter 1, pp. 27–51, 1983.
Weder, Hans Georg, Othmar Zumbuehl (1985) "The Preparation Of Variably Sized Homogenious Liposomes For Laboratory, Clinical, and Industrial Use By Controlled Detergent Dialysis" Liposome Technology, Chapter 7, CRC Press, Boca Raton, Florida (US), pp. 79–107.
Laurence, J. (1990) "Review: Novel Vaccination and Antireceptor Strategies Against HIV," *AIDS Res. and Human Retroviruses*, vol. 6, No. 2, Mary Ann Liebert, Inc. Publishers, Cornell University Medical College, N.Y.
Ho, R. J. Y., R. L. Burke, R. C. Merigan (1989) "Antigen-Presenting Liposomes are Effective in Treatment of Recurrent Herpes Simplex Virus Genitalis in Guinea Pigs," J. Virology 63(7):2951–2958.
El Guink, N., R. M. Kris, G. Goodman-Snitkoff, P. A. Small, Jr., R. J. Mannino (1988) "Intranasal immunization with proteoliposomes protects against influenza," Vaccine 7:147–151.
Gould-Fogerite, S., J. E. Mazurkiewicz, D. Bhisitkul, R. J. Mannino (1988) "The Reconsititution of Biologically Active Glycoproteins into Large Liposomes: Use as a Delivery Vehicle to Animal Cells," *Advances in Membrane Biochemistry and Bioenergetics*, Plenum Press, N.Y., pp. 569–586.
Nussbaum, O., M. Lapidot, A. Loyter (1987) "Reconstitution of Functional Influenza Virus Envelopes and Fusion with Membranes and Liposomes Lacking Virus Receptors," J. Virol. 61(7):2245–2252.
Haddad, R. S., L. M. Hutt-Fletcher (1989) "Depletion of Glyocprotein gp85 from Virosomes Made with Epstein-Barr Virus Proteins Abolishes Their Ability to Fuse with Virus Receptor-Bearing Cells," J. Virol. 63:4998–5005.
Oth, D., G. Mercier, P. Perrin, M. L. Joffret, P. Sureau, L. Thibodeau (1987) "The Association of the Rabies Glycoprotein with Liposome (Immunosome) Induces an in Vitro Specific Release of Interleukin 2," Cellular Immunology 108:220–226.
Thibodeau, L., M. Chagnon, L. Flamand, D. Oth, L. Lachapelle, C. Tremblay, L. Montagnier (1989) "Role of liposomes on HIV envelope glycoprotein presentation and immune respone in mice," C. R. Adac. Sci. Paris 309(III): 741–747.

*Primary Examiner*—Thurman K. Page
*Assistant Examiner*—G. S. Kishore
*Attorney, Agent, or Firm*—Saliwanchik & Saliwanchik

[57] ABSTRACT

The production of artificial viral envelopes by a novel double-detergent dialysis technique is disclosed. Specifically exemplified is the production of HIV-1 and RSV viral envelopes. The resulting artificial viral envelopes are essentially identical to the natural virus with regard to characteristics which are relevant to immunogenicity.

5 Claims, No Drawings

ARTIFICIAL VIRAL ENVELOPES

This application is a continuation, of application Ser. No. 07/600,641, filed Oct. 19, 1990 now abandoned.

BACKGROUND OF THE INVENTION

Enormous efforts are currently being made to develop a vaccine against HIV-1 (Laurence, J. [1990] AIDS Res. 6:175-181). Currently tested systems employ either killed virus, stripped of its coat, or one of the HIV proteins, either surface glycoproteins (gp120, gp160) or core proteins (p24, hgp30). The main limitation with subunit protein vaccines is their poor immunogenicity, even if combined with an adjuvant, e.g., muramyltripeptide or others.

Another approach, used by several investigators, has been to enhance the immunogenic activity of subunit vaccines by preparing protein-containing lipid vesicles, called "proteoliposomes," "immunoliposomes," "immunosomes," "virosomes," or the like. Methods to prepare these vesicles vary widely, however, they are based on one of the following protocols: proteins are usually (i) passively bound to lipids by van der Waal's or hydrophobic interaction; (ii) covalently bound to lipids, or to phospholipid molecules (mainly phosphatidylethanolamine), via divalent coupling agents such as SPDP and others; or (iii) reconstituted with extracted viral lipids, phospholipids, or a combination of both, from detergent-solubilized lipid-protein mixtures.

Only a small number of investigators (Ho, R. J. Y., R. L. Burke, T. C. Merigan [1989] J. Virology 63:2951-2958; El Guink, N., R. M. Kris, G. Goodman-Snitkoff, P. A. Small Jr., and R. J. Mannino [1989] Vaccine 7:147-151; Gould-Fogerite, S., J. E. Mazurkiewicz, D. Bhisitkul, and R. J. Mannino [1988] In *Advances in Membrane Biochemistry and Bioenergetics* [C. H. Kim et al., eds.] Plenum Press, New York, pp. 569-586; Nussbaum, O., M. Lapidot, and A. Loyter [1987] J. Virol. 61:2245-2252; Haddad, R. S., and L. M. Hutt-Fletcher [1989] J. Virol. 63:4998-5005; Oth, D., G. Mercier, P. Perrin, M. L. Joffret, P. Sureau, and L. Thibodeau [1987] Cell. Immunol. 108:220-226; Thibodeau, L., M. Chagnon, L. Flamand, D. Oth, L. Lachapelle, C. Tremblay, and L. Montagnier [1989] C. R. Acad. Sci. Paris 309(III):741-747) made an effort to insert proteins so that binding and/or immunogenicity was retained upon reconstitution of the mixture, usually via detergent dialysis. However, in most cases, arbitrary phospholipid mixtures are used which do not represent the accurate lipid composition of the viral envelope. Only El Guink et al. (1989, supra) used control piposomes (without viral proteins) similar to the natural viral lipid composition.

Thibodeau et al. (1989, supra) describe a method of "anchoring" HIV gp160 on the surface of liposomes to prepare "HIV-immunosomes." However, the liposome composition is not disclosed, and the "anchoring" is achieved by simple incubation of preformed liposomes with the purified gp160.

In contrast to Thibodeau et al.'s (1989, supra) approach, we have generated a viral envelope identical to the HIV-1 envelope with respect to its lipid composition, an approximately equimolar lipid:cholesterol ratio, unilamellarity, and vesicular size. Furthermore, the incorporation of gp160 was achieved by partial resolubilization of the lipid envelopes in order to maintain the correct three-dimensional protein conformation by incorporation of the hydrophobic gp41 part of gp160 into the lipid envelope. Using our innovative approach, it is now possible to formulate subunit vaccines which are superior to conventional vaccines.

The subject invention, which utilizes a unique double-detergent dialysis procedure, results in a viral envelope with proteins only on the surface, as they should be, rather than randomly intermingled with the envelope lipid portion.

BRIEF SUMMARY OF THE INVENTION

Disclosed are novel artificial viral envelopes, essentially identical to natural viral envelopes, e.g., to the human immunodeficiency virus (HIV-1), the respiratory syncytial virus (RSV), or other viruses, and a novel method, double-detergent dialysis, essential to prepare same.

Natural viral envelopes are unique in their cholesterol:phospholipid ratio of about 0.8–1.2 and, until now, could not be reproduced by any known preparation technique.

The subject invention describes a novel method, double-detergent dialysis, which can be used to prepare lipid vesicles in general and viral envelopes in particular. The first step of the novel process is the preparation of lipid vesicles without glycoprotein from a detergent-solubilized lipid mixture at a unique lipid:detergent ratio. Next, glycoproteins are inserted into the preformed vesicles by partial micellation with another detergent followed by dialysis. The process has been adapted to reproducibly yield both small (<5 ml) laboratory scale samples as well as sterile large batches (>100 ml). An important aspect of this method is that the two steps are independent process. Thus, a large reservoir of concentrated lipid envelopes can be prepared and stored while individual batch sizes of the final envelope containing the surface protein, or the desired composite epitopes of surface proteins, can be prepared upon demand.

The artificial viral envelopes can be characterized by: (i) an advantageous phospholipid:cholesterol ratio of about 1:1; (ii) a virus-specific phospholipid composition; (iii) a homogenous size distribution around 250 nm, similar to natural viral size; (iv) a uniquely stable, rigid, unilamellar structure; (v) envelope glycoproteins such as the HIV-1 gp160, RSV G (aggregation) and F (fusion) proteins, and others, inserted in the outer surface; (vi) high fusogenic activity; (vii) specific binding to their monoclonal antibodies confirming the intact conformation of the surface glycoproteins; and (viii) selective binding to cell surface receptors such as the CD4 receptor on human T-cells.

The following applications of the artificial viral envelopes are proposed: (i) synthetic subunit vaccines; (ii) highly targetable and fusogenic drug delivery devices for delivery of antiviral agents to infected cells; (iii) highly specific cell destructing agent; (iv) non-biohazard in vitro model systems for viral infectivity; and (v) highly efficient transfection device for the introduction of genetic materials into animal, bacterial, and plant cells.

DETAILED DESCRIPTION OF THE INVENTION

The artificial lipid vesicles of the subject invention are characterized by: (i) a cholesterol:phospholipid ratio of about 0.8 to about 1.2, similar to that of natural viral envelopes; (ii) a phospholipid composition similar to the natural phospholipid mixture of viral envelopes; (iii) a homogenous size distribution in the range of about 50 to about 500 nm, which is similar to that of the natural viral particle; and (iv) a physically stable unilamellar membrane structure. In one preferred embodiment of the invention, the novel lipid vesicles may be further characterized by (v) envelope proteins such as the HIV-1 gp160, RSV G (aggregation) and F (fusion) proteins, and others, inserted in the outer surface; (vi) high fusogenic activity; (vii) specific binding to their monoclonal antibodies confirming the intact conformation of the surface proteins following insertion; and (viii) selective binding to cell surface receptors such as the CD4 receptor on human T-cells.

Preferably, the phospholipid composition of the synthetic viral envelopes should be similar to the natural viral composition and should comprise phosphatidylcholine (PC), phosphatidylserine (PS), phosphatidylethanolamine (PE), and sphingomyelin (SM). The envelope may further comprise additional lipids such as phosphatidylinositol.

The artificial lipid vesicles are prepared by a novel method—double detergent dialysis. As specifically exemplified herein, this method consists essentially of two steps: (1) preparation of the phospholipid/cholesterol envelope by solubilization of the lipids and cholesterol with sodium cholate or other appropriate detergent as the solubilizing agent at a unique molar ratio of approximately 45:1, followed by removal of the detergent by exhaustive dialysis against phosphate-buffered saline (PBS); and (ii) insertion of protein(s) in the outer surface of the preformed vesicles by partial micellation with sodium deoxycholate or other appropriate detergent at an approximate ratio of 8:1 and removal of the detergent by exhaustive dialysis as before in step (i). The method of the subject invention can be readily modified by a person skilled in the art to use, for example, other solubilizing agents or buffers. Generally, the proteins which are inserted into the preformed vesicles will be glycoproteins but other proteins can be used, so long as they remain inserted in the lipid vesicle.

The detergent:lipid ratio can be from about 10:1 to about 100:1 and is preferably from about 30:1 to about 60:1 and is most preferably approximately 45:1. For the second dialysis step, the detergent:lipid ratio can be from about 1:1 to about 20:1 and is preferably from about 5:1 to about 10:1 and is most preferably about 8:1. Useful detergents are well known to those skilled in the art and include, but are not limited to, bile salts (sodium cholate, deoxycholate, taurocholate, etc.), CHAPSO, octylglucoside, TRITON-X derivatives, etc. Dialysis and related methodologies can be carried out using any of a number of techniques which are known to those skilled in the art. For example, bag, disc, flow-through, and counter-flow dialysis techniques and apparatus may be utilized. A wide range of lipid:protein molar ratios can be used. This range may be, for example, from about $1 \times 10^6:1$ or higher to around 100:1 or lower. The ultrastructure should preferably be unilamellar, however, oligolamellar may also be acceptable for some purposes.

An important aspect of the double-detergent dialysis method is that the two steps are independent processes. During the first step, unilamellar lipid envelopes in a size range of about 50 to about 500 nm or, preferably, about 150 to about 350 nm or, most preferably, approximately 250 nm, essentially identical to natural viral membranes, are generated. These preformed envelopes are of superior physical stability with an average size, and size distribution, that remain essentially unchanged over several months when stored under refrigeration.

The envelopes produced according to the subject invention can be freeze-dried and thus preserved for extended periods of time. The freeze-drying, or other means of preservation, can be done either before or after insertion of the protein onto the envelope. The use of freeze-drying procedures can reduce or eliminate the need for keeping vaccines refrigerated and, therefore, can be very important for field uses, especially in underdeveloped countries. The stability of the lipid vesicles can be improved even further by polymerization of one or more of the phospholipid components.

Thus, a large reservoir of concentrated lipid envelopes can be prepared and stored while individual batch sizes of the final artificial viral envelope containing the surface protein or their desired composite epitopes can be prepared upon demand. The method is flexible so that batch sizes in a range of less than 5 ml to liter quantities can be prepared reproducibly and under sterile conditions using, for example, either teflon dialysis cells or flow-through hollow fiber dialysis apparatus.

An important feature of the viral envelopes produced according to the subject invention is that the protein can be inserted only on the outside surface of the envelope. Whole proteins or antigenic determinants or epitopes may be used on the lipid vesicle. As used herein the terms "epitopes" and "determinants" are used interchangeably to refer to portions of proteins or peptides which either raise antibodies or are recognized by or react with antibodies. Advantageously, this protein is exposed and available for antigenic and immunologic reactivity. The protein which is applied to the envelope may be natural protein isolated from any viral, bacterial, or other source. Also, the protein may be produced through recombinant means. The recombinant protein may be, for example, reactive epitopes from a virus of interest. Also, the protein applied to the envelope may be a cocktail of proteins or epitopes from a single virus (or other entity) or from several viruses (or other entities). The novel envelopes can be actively targeted to specific cells via receptor recognition, e.g., CD4 receptor; at the same time, they are naturally targeted to macrophages which in many cases are reservoirs for viral and bacterial diseases. In addition, viral core proteins may be entrapped within the artificial envelopes which may further enhance their immunogenic response.

According to the subject invention, the lipid envelopes produced according to the unique process can be coated with proteins from any one of a number of viruses, bacteria, and parasites. Specifically exemplified herein is the construction of artificial RSV and HIV-1 envelopes. The following applications of an artificial HIV-1 viral envelope can be envisioned:

1. Artificial HIV-1 envelopes, being identical to the natural HIV-1 envelopes in size and chemical composition, would induce both a humoral and cellular immune response; thus, they may serve as a synthetic subunit vaccine against HIV-1. Several significant advantages of such a synthetic vaccine over vaccination with a natural modified HIV preparation can immediately be appreciated: (a) since the artificial HIV-1 envelope is void of genetic information, there is no danger of infection; (b) the synthetic vaccine is likely to be more immunogenic due to proper presentation of the antigen to lymphocytes; (c) insertion of desired composite epitopes will yield highly efficacious vaccines; and (d) antigenic drift, once identified and reproduced by recombinant techniques, can immediately be simulated with the synthetic vaccine.

2. Due to the unique capability of the HIV-1 virus to bind to and fuse with CD4+ cells, the artificial HIV-1 envelope may be utilized as a novel "target-seeking" drug delivery system for antiviral drugs for delivery of antiviral agents specifically to HIV-1 infected cells. This is an important and novel aspect of the artificial HIV-1 envelope since both the antiviral killing efficacy of antiviral drugs and stimulation of production of virus-neutralizing antibodies can be combined in the same delivery device in order to effectively protect an infected individual from spreading of the infection and provide a potential cure of the disease.

3. The investigation of biochemical and immunological pathways as well as the development of vaccines and antiviral drugs is complicated by restrictive regulations necessary to protect personnel from inadvertent exposure to HIV-1. Since the artificial HIV-1 envelope does not contain genetic information, its use would be much less restricted. Therefore, the artificial HIV-1 envelope may serve (a) as an in vitro model for viral infectivity, particularly to investigate viral cell binding and cell fusion, and (b) as an in vitro efficacy screening test of antiviral drugs that act on the principle of viral membrane perturbation or specific binding to viral surface proteins.

Artificial RSV envelopes may serve as a synthetic vaccine against RSV in a similar fashion as described above for HIV-1. In addition, it may serve as a drug delivery system for antiviral agents such as ribavirin and others for the treatment of pulmonary RSV infections. Artificial RSV envelopes are highly fusogenic and, therefore, may be used as an efficient fusogenic intracellular drug carrier, specifically for the aerosol delivery of antiviral drugs to infection sites in lung epithelial cells.

A virtually unlimited number of artificial viral envelopes can be prepared and applied as described for the examples above using recombinant or isolated surface determinants. For example, the novel lipid vesicles of the subject invention can be used in connection with a number of human viruses including arboviruses including alphaviridae (Easter, Western, and Venezuelan equine encephalitis virus), flaviviridae (St. Louis encephalitis virus), bunyaviridae (California encephalitis virus), orbivirus (Colorado tick fever), yellow fever virus, Dengue and Dengue hemorrhagic fever virus, Japanese encephalitis virus, Murray Valley encephalitis virus, Chikungunya virus, tick-borne encephalitis virus, Kyasanur Forest virus, Crimean hemorrhagic fever and Congo virus, Rift Valley Fever virus; arenaviruses including lymphocytic choriomeningitis virus, Argentinean and Bolivian hemorrhagic fever virus, and Lassa fever virus; coronaviruses including infectious bronchitis virus; human cytomegalovirus; enteroviruses including polioviruses, Coxsackieviruses A and B, echoviruses, and hepatitis A virus; Epstein-Barr virus; gastroenteritis-causing viruses including Norwalk group of viruses and rotaviruses; bunyaviruses including hantaviruses (hemorrhagic fever with renal syndrome); hepatitis viruses including A, B, delta, non-A-non-B; herpes simplex viruses 1 and 2; varicella zoster virus (human herpes virus 3); influenza virus (A,B,C); paramyxoviruses including parainfluenza virus type 1-3; respiratory syncytical virus; measles virus; mumps virus; rabies and rabies-related viruses; retroviruses including human T-lymphotrophic virus type I and II (HTLV-I/II) and human immunodeficiency virus type 1 and 2 (HIV-½); rhinoviruses; rubella virus; orthopoxvirus group including smallpox virus; B19 parvovirus; human papilloma viruses; Newcastle disease virus; Semliki Forest virus; encephalomyocarditis virus; Marburg and Ebola virus (African hemorrhagic fever); vesicular stomatitis virus; DNA viruses including adenoviruses (41 types) (Acute Respiratory Disease ARD); natural, complete, truncated or synthetic viral glycoproteins and chimeras thereof, viral proteins and peptides used to prime MHC class-I-restricted and class-II-restricted cytotoxic T lymphocytes (CTLs); viral protein fragments (e.g., from RSV G glycoprotein) which induce T helper and B cells and chimeras thereof.

This technology can also be used with animal viruses such as bovine viral diarrhea virus, hog cholera virus, border disease virus (sheep); infectious bursal disease virus (chicken), Sindbis virus (equine encephalitis); canine distemper virus, phocid distemper virus, rinderpest virus, peste des petits ruminants virus, foot-and-mouth disease virus, feline immunodeficiency virus, simian immunodeficiency virus, bovine leukemia virus.

Epitopes from bacterial and parasitic disease agents such as *Corynebacterium diphtheriae* (diphtheria), *Clostridium tetani* (tetanus), *Neisseria meningitidis* (meningitis), *Streptococcus pneumoniae* (pneumonia), *Haemophilis influenzae* (meningitis) (capsular polysaccharides), *Bordatella pertussis* (whooping cough) (pertussis toxin), *Salmonella typhi* (typhoid fever), *Vibrio cholerae*, *Coxiella burnetii* (Q fever), *Mycobacterium tuberculosis*, atypical mycobacteria including *M. avium-intracellulare* and *M. kansasii*, Shigella, *leishmaniasis, schistosomiasis, Plasmodium falciparum* (malaria), *Eimeria* (coccidiosis) (poultry) can also be used with the novel envelopes.

These novel lipid vesicles of the subject invention can also be used to transfer genetic material to bacterial cells, yeasts, animal and human cells, or plant cells. As used herein, "genetic material" refers to gene constructs, DNA, RNA, or plasmids. The genetic material may be incorporated into the lipid vesicle during the first step of the novel process such that the genetic material is encapsulated within the lipid vesicle. Artificial lipid vesicles could be used in plants as vectors carrying t-DNA for the transfer of host-defense response genes; or to create host "resistance" genes, e.g., import *Bacillus thuringiensis* crystal-protein gene to express *B. thuringiensis* toxin as "bioinsecticide;" or to deliver anti-sense nucleic acid, e.g., anti-sense construct of polygalacturonase in tomato plants; or to deliver viral satellite RNA; or to deliver ribozymes to induce autocatalytic RNA cleavage, e.g., of the satellite tobacco ringspot virus RNA. Viral envelopes may be from the groups of reoviruses, robemoviruses, tymoviruses, tombusviruses, inteoviruses, tobraviruses, furoviruses, comoviruses, nepoviruses, hordeiviruses, cucomoviruses, ilarviruses, bromoviruses, alfalfa mosaic virus, rice stripe virus, tomato spotted wilt virus, velvet tobacco mottle viruses.

In addition to their uses as subunit vaccines and vectors, the envelopes described herein can be used in a variety of therapeutic applications including the destruction of viruses or specific cells such as cancer cells. Also, these envelopes can be appropriately modified to play a role in the modulation of biological pathways or reactions, especially in the endocrine and immune systems. These envelopes can be targeted to T-cell lymphocytes and their subpopulations. Advantageously, receptor-specific drug/toxin modulator delivery systems can be tailored to any receptor that recognizes peptide or protein moieties that can be inserted in the viral envelope.

The use of the lipid vesicles of the subject invention to deliver drugs, toxins, or other substances can be accomplished in at least two ways. First, the lipid vesicle may be constructed to encapsulate the drug or toxin of interest. The vesicle could then be coated with a protein determinant which directs the lipid vesicle (and encapsulated substance) to the desired location. Alternatively, the lipid vesicle may be conjugated to any number of moieties. For example, the lipid vesicle may be conjugated to a toxin by coating the vesicle with glycoproteins which act as spacer arms to connect the lipid vesicle to the toxin. These glycoproteins which are embedded in the lipid vesicle may have, for example, a cysteine residue at the free end of the protein which would facilitate conjugation to a toxin via a disulfide bond.

The technology described herein can be used to treat various diseases including, but not limited to, T-cell malignancies related to retrovirus activity such as acute lymphoblastic leukemia, Kawasaki's disease, Hodgkin's disease; sarcoidosis; neurological syndromes including multiple sclerosis and chronic neurological diseases including subacute sclerosing panencephalitis, progressive multifocal leukoencephalopathy, Kuru and Creutzfeldt-Jakob disease; autoimmune diseases including degenerative joint disease. Cancers with known viral agents include cervical cancer (herpes simplex virus 2, human papilloma virus); Burkitt lymphoma (Epstein-Barr virus); nasopharyngeal carcinoma (Epstein-Barr virus); hepatocellular carcinoma (hepatitis B virus).

The drugs and other active agents that these envelopes can be used with include antiviral, antibiotic, and antifungal drugs. Also, the envelopes can be linked to toxins, polynucleotides, immunomodulators, and membrane-perturbing agents.

The compositions of the subject invention can be delivered to humans or animals by a number of methods known to those skilled in the art. For example, the lipid vesicles may be formulated for parenteral, oral, or topical administration. Also, in a preferred embodiment of the invention, the compounds may be administered as an aerosol spray or as nasal or ocular drops. The formulations will typically be in a saline/buffer solution.

MATERIALS USED

Phospholipids were purchased from the following sources; egg phosphatidylcholine (PC) (lot #37F-8420), phosphatidylserine (PS) (lot #99F-83561) from bovine brain, egg phosphatidylethanolamine (PE) (lot #58F-8371), cholesterol from porcine liver (lot #36F-7040), deoxycholic acid (lot #108F-0331) and sodium cholate (lot #78F-0533) were from Sigma Chemical Co., St. Louis, Mo. Egg sphingomyelin (SM) (lot #ESM-22) was from Avanti Polar Lipids, Pelham, Ala. The composition of phosphate buffered saline (PBS) was NaCl 137 mM, KCl 2.7 mM, Na$_2$HPO$_4$ 8.1 mM, KH$_2$PO$_4$ 1.5 mM, with 0.5 mM sodium azide (lot #13F-0600) (Sigma). Spectra/Por 2 (mol. cut-off 12–14,000) membrane discs were used for dialysis in teflon dialysis cells.

HIV-1 gp160 envelope protein (lot #8962R-1) at a concentration of 100 µg/ml in 5 mM Tris buffer containing 0.005% polysorbate 20 was from MicroGeneSys, Inc., West Haven, Conn. According to the manufacturer's specifications, it is a full-length glycosylated recombinant protein derived from the env gene of HIV-1. The protein is produced in insect cells using the baculovirus expression system and purified by low pressure, low temperature chromatography.

RSV glycoproteins F and G were obtained from Dr. E. Walsh, Rochester, N.Y., and were purified by affinity chromatography according to published methods. Purity was assessed by SDS polyacrylamide gel electrophoresis and Coomassie Blue stain. Western blots showed no cross-reactivity of F glycoprotein with G glycoprotein and vice versa.

HEp-2 cells were grown on sterile coverslip flasks at 37° C. and 5% CO$_2$. When the cells were approximately 50% confluent, they were washed with PBS and then used to perform fusion experiments.

The following examples illustrate and exemplify the objectives and embodiments of the present invention. However, the invention is in no way restricted to the examples presented.

EXAMPLE 1

Preparation of Artificial HIV-1 or RSV Envelopes (Without Protein)

Stock lipid solutions were prepared as shown in Table 1. Briefly, enough cholesterol or phospholipids were dissolved individually in 10 ml chloroform to give the concentrations indicated in Table 1. Sodium cholate stock solution was prepared in methanol.

TABLE 1

| Lipid Composition and Stock Solutions | | | | |
|---|---|---|---|---|
| | mg/10 ml HCCl$_3$ | MW | µmoles/ 10 ml | mole % of total PL |
| cholesterol (CH) | 38 | 386 | 98.4 | |
| phosphatidylcholine (PC) | 20 | 786 | 25.4 | 23.7 |
| phosphatidylethanolamine (PE) | 18 | 743 | 24.2 | 22.6 |
| phosphatidylserine (PS) | 23 | 832 | 27.6 | 25.7 |
| sphingomyelin (SM) | 22 | 731 | 30.1 | 28.1 |
| TOTAL PHOSPHOLIPID (PL) | 83 | | 107.3 | 100.0 |
| TOTAL LIPID (incl. CH) | 121 | | 205.7 | |
| Sodium cholate | 2000[1] | 430.6 | 4644.7 | |

[1] in methanol

As shown in Table 2, the ratio of total phospholipid:cholesterol was approximately 1, and the detergent:total lipid ratio was approximately 45.

TABLE 2

| Lipid:Cholesterol and Lipid:Detergent Ratio | | |
|---|---|---|
| CONC. (µMOLE/10 ml) | | MOLAR RATIO |
| Total Phospholipid | Cholesterol | |
| initial | | |
| 107.3 | 98.4 | 0.92 |
| recovered after dialysis | | |

TABLE 2-continued

| Lipid:Cholesterol and Lipid:Detergent Ratio | | |
|---|---|---|
| CONC. (μMOLE/10 ml) | | MOLAR RATIO |
| 79.4 (74.0%) | 69.2 (70.3%) | 0.87 |
| Total Lipid | Sodium Cholate[1] | |
| 205.7 | 9289.4 | 45.2 |

[1]Total amount of detergent used: 4 mg (20 μl) = 9289.4 μmoles

The phospholipid composition of artificial and natural HIV-1 envelopes (Gordon, L. M., F. C. Jensen, C. C. Curtain, P. W. Mobley, R. C. Aloia (1988) In *Lipid Domains and the Relationship to Membrane Function* [R. C. Aloia et al., eds.] Alan R. Liss, Inc., New York, pp. 225-294) is shown in Table 3. The minor fractions of 2.1 mole % phosphatidylinositol and 0.9 mole % phosphatidic acid, and the 5 mole % of "other" lipids (Gordon et al., supra) were substituted by a larger fraction (25.7 mole % vs. 15.1 mole % in the natural membrane of PS.

TABLE 3

| Lipid Composition of Artificial and Natural HIV-1 Envelope | | | | | | | |
|---|---|---|---|---|---|---|---|
| | MOLE % OF TOTAL PHOSPHOLIPIDS | | | | | | |
| LIPID | PC | PE | SM | PS | PI[2] | PA[3] | Other |
| NATURAL[1] | 23.8 | 24.6 | 28.3 | 15.1 | 2.1 | 0.9 | 5.0 |
| ARTIFICIAL | 23.7 | 22.6 | 28.1 | 25.7 | n.a.[4] | n.a. | n.a. |

[1]Gordon, L. M. et al., supra
[2]PI = phosphatidylinositol
[3]PA = phosphatidic acid
[4]n.a. = not added Of every lipid stock solution, 500 μl were combined in a round-bottom flask and 1000 μl of the sodium cholate stock solution were added. The organic solvent was removed under a stream of nitrogen.

The lipid/detergent film was dispersed in 5.0 ml 10 mM PBS and sonicated for 10 minutes in a bath sonicator (Lab Supplies, Hicksville, N.Y.) until solubilization of the lipids was completed. The clear liquid was transferred to a teflon dialysis cell equipped with a Spectra/Por 2 membrane (MW cut-off 12-14,000) and dialyzed against 2 liters of PBS with 5 buffer changes after 4, 8, 16, 24, and 48 hours. The buffer was purged with $N_2$ over the entire time of dialysis. The samples were removed form the dialysis cell after a total dialysis time of 54-56 hours and stored at 4° C.

The size and size distribution of the artificial envelopes was analyzed using a NICOMP Model 370 laser particle sizer (Particle Sizing Systems, St. Barbara, Calif.). A typical example of a homogenous population of vesicles had an average size of 216 nm±82 nm (Std. Dev.) and a chi[2] value of 1.39. The reproducibility of preparation was remarkable. A total of 15 samples prepared was found to have an average diameter of 250 nm with an extremely narrow standard deviation of the means of 26 nm.

The ultrastructure of the vesicles was determined by freeze-fracture electron microscopy. The results of the electron microscopy showed perfectly unilamellar artificial envelopes.

Cholesterol was determined according to the method of Zlatkis et al. (Zlatkis, A., B. Zak, and A. J. Boyle [1953] *J. Lab. Clin. Med.* 41:486-492). A total of 267.1 μg CH/ml, corresponding to 76.3% of the original total amount of CH, were recovered.

For phospholipid analysis a sample was extracted according to the method of Bligh and Dyer (Bligh, E. G., and W. J. Dyer [1959] *Can. J. Biochem. Phys.* 37:911-917). A quantitative phospholipid assay was performed according to the method of Stewart (Stewart, J. C. M. [1980] *Anal. Biochem.* 104:10-14). In a typical experiment, a total of 613.8 μg PL/ml, corresponding to 74.0% of the original total amount of PL, was recovered.

The final phospholipid:cholesterol ratio was 0.87, only slightly different than the original ratio of 0.92.

EXAMPLE 2

Stability of Artificial HIV Envelopes (Without Protein)

Artificial HIV-1 envelopes (without protein) were stored at 4° C. in the refrigerator. Average size and size distribution were analyzed periodically by laser light scattering. Surprisingly, it was found that these envelopes were extremely stable with respect to retention of their original size. Examples of the size retention of four different batches stored over 20, 30, 60, 69, and 163 days, respectively, are shown in Table 4. Such practically ideal physical stability was a completely unexpected finding, since it is known that conventional liposomes of a comparable size and high cholesterol content "grow" upon storage due to the high free energy content of the highly curved membranes.

TABLE 4

| Physical Stability of Artificial HIV-1 Envelopes | | | | |
|---|---|---|---|---|
| Time from Prep. (days) | Average Size (nm) ± Size Distribution | | | |
| | Sample 1 | Sample 2 | Sample 3 | Sample 4 |
| 0 | 267 ± 137 | 216 ± 82 | 274 ± 106 | 234 ± 99 |
| 2 | 264 ± 123 | | | |
| 4 | | 211 ± 77 | | |
| 6 | 253 ± 111 | | | |
| 7 | | 208 ± 87 | | |
| 8 | 239 ± 92 | | | |
| 15 | | 209 ± 89 | | |
| 15 | | 181 ± 48[1] | | |
| 17 | 252 ± 95 | | | |
| 20 | | 190 ± 57[1] | 247 ± 94 | |
| 30 | | 195 ± 58[1] | | |
| 60 | | | | 283 ± 112 |
| 69 | 285 ± 42 | | | |
| 163 | | | | 286 ± 91 |

[1]After the first reading on day 15, this sample was filtered through a 0.22 μm Acrodisc (Gelman) filter.

EXAMPLE 3

Preparation of Artificial HIV-1 Envelopes with gp160

Complete artificial HIV-1 envelopes containing the HIV-1 gp160 were prepared by a novel double-detergent dialysis technique. Double-detergent dialysis is a requirement because the high concentration of cholesterol in the lipid envelope requires a high concentration of detergent. Therefore, the dialysis is performed in two steps. The first step of preparing the lipid envelopes without the protein was essentially identical to the procedure described in Example 1, above. The second dialysis step consisted of the following procedure: The preformed envelopes were filtered through 0.22 μm filters (Acrodisc) and 2.5 ml of these were mixed under aseptic conditions with 0.5 ml of a filtered aqueous solution of deoxycholate detergent:lipid molar ratio ≈ 8) and incubated at room temperature for 1 hour. Partial solubilization was observed with electron microscopy of a vesicle sample treated similarly. gp160 (100 μg) was added aseptically, gently mixed, and kept for 45 minutes at room temperature. The mixture was then dialyzed in the cold (4° C.) against 2 liters of Tris (10 mM, pH 7.8, containing 0.5 mM NaN₃) with 5 buffer changes at 4, 8, 16, and 48 hours. The buffer was purged with $N_2$ for the entire time of dialysis. The sample was removed after 56 hours and analyzed for size and inclusion of gp160 on the outer vesicle surface by immunolabeling followed by electron microscopy (see Example 4).

EXAMPLE 4

Immunolabeling and Determination of gp160 on the Surface of Artificial Envelopes Formvar coated nickel grids were treated with a 1% solution of poly-L-lysine for 10 minutes, briefly washed in water, and placed on a drop of the artificial envelopes. Envelopes were allowed to adsorb to the surface of the grid for one minute. Grids were floated on PBS for 10 minutes, followed by 10 minutes on 1% bovine serum albumin (BSA). After removal of excess BSA, the grids were incubated for 1 hour on a 1:250 dilution of the monoclonal antibody specific to gp160 (Cellular Products, Inc., Buffalo, N.Y.) or on an irrelevant monoclonal antibody. Grids were washed three times for 10 minutes each on PBS and incubated on a 1:20 dilution of goat anti-mouse IgG coupled to 15 nm colloidal gold for 1 hour. Grids were washed twice for 10 minutes in each PBS and distilled water. Grids were negatively stained with 1% uranyl acetate in water for 20 seconds, drained, and allowed to dry. The grids were observed on a Hitachi H-7000 electron microscope at 70 kV. Control lipid envelopes without protein were treated in an identical manner.

Monoclonal anti-gp160 antibody was found bound specifically to viral envelopes as visualized with the anti-mouse IgG-coupled gold, whereas viral envelopes treated with unrelated monoclonal antibody and lipid envelopes without protein treated with anti-gp160 antibody and the gold stain did not show gold-antibody binding.

EXAMPLE 5

Selective Binding of Artificial Envelopes to CD4+ Cells

L. W. cells were derived at the University of Florida from the peripheral blood of a patient with HTLV-1 positive adult T-cell acute lymphoblastic leukemia. Flow cytometry analysis demonstrated these cells as 90–100% positive for the CD4 surface antigen. The HL-60 cell line was obtained from ATCC, Rockville, Md. These cells are grown in suspension culture and have myeloblast/promyelocyte morphology. They lack specific markers for lymphoid cells. Approximately $1 \times 10^6$ cells in 0.5 ml were centrifuged at 1,000 xg for 10 minutes; 10 μl of [$^{125}$I]-labeled envelopes, corresponding to $\approx 1 \times 10^6$ cpm (TCA-precipitate = $\approx 54\%$ of total counts), were added, and incubated on ice for 1 hour; 0.6 ml PBS were added; the sample was centrifuged, the pellet washed 5 times with PBS and bound $^{125}$I (cpm) counted in a gamma counter.

As shown in Table 5, counts associated with the CD4+ L. W. cells were significantly higher than counts bound to CD4− control cells. This confirms the presence and conformational integrity of the gp160 on the artificial membrane surface and its affinity to the CD4 receptor.

TABLE 5

| Selective binding of artificial envelopes to CD4+ cells | | |
|---|---|---|
| Cell Type | CD4 | [$^{125}$I] Binding (cpm) Avg. ± Std. (N = 3) |
| L.W. | + | 134,994 ± 20,529 |
| HL-60 | − | 82,614 ± 13,155 |

EXAMPLE 6

Preparation of Artificial RSV Envelopes with G and F Glycoproteins

Artificial RSV envelopes were prepared essentially identical to the method described in Example 1 and Example 3. Glycoprotein stock solutions contained 175 $\mu$g/ml G glycoprotein (MW $\approx$ 90,000) and 350 $\mu$g/ml F glycoprotein (MW $\approx$ 48,000), respectively.

Four samples of 1 ml lipid stock solution corresponding to 1.21 mg or 20.6 $\mu$mole total lipid were removed and dried under a stream of $N_2$ prior to redispersion and solubilization with sodium cholate followed by dialysis (Example 1). Since these samples were used to demonstrate fusogenicity of the artificial RSV envelopes, the fluorescent dye 6-carboxyfluorescein (6-CF) was added as aqueous space marker. A sample of nonspecific artificial envelopes without glycoprotein was used as control in fusion experiments (Example 7). In step 2, one sample was prepared with 46.3 $\mu$l of the G glycoprotein stock solution only, one sample with 8.2 $\mu$l of the F glycoprotein stock solution only, one sample with both 46.3 $\mu$l of the G glycoprotein and 8.2 $\mu$l of the F glycoprotein stock solution. Deoxycholate was added and the samples processed as described in Example 3. The corresponding lipid:protein ratios are shown in Table 6. Prior to use in fusion tests (see Example 7) the artificial RSV envelopes were centrifuged for 10 minutes in an Eppendorff microfuge and the CF solution replaced with PBS.

TABLE 6

Lipid:Protein Ratio of Artificial RSV Envelopes

| Glycoprotein | Lipid Conc. ($\mu$mole/ml) | Glycoprotein Conc. ($\mu$mole/ml) | Molar Ratio |
|---|---|---|---|
| G | 20.6 | $9 \times 10^{-5}$ | $2.3 \times 10^5$ |
| F | 20.6 | $6 \times 10^{-5}$ | $3.4 \times 10^5$ |
| G + F | 20.6 | $1.5 \times 10^{-4}$ | $1.4 \times 10^5$ |

EXAMPLE 7

Fusion of Artificial RSV Viral Envelopes With HEp-2 Cells

HEp-2 cells were grown on sterile coverslip flasks at 37° C. and 5% $CO_2$. When the cells were approximately 50% confluent, they were washed with PBS and then used to perform fusion experiments as follows: To HEp-2 cells in Petri dishes were added 0.5 ml of one of the solutions containing the artificial envelopes without protein, with G glycoprotein only, with F glycoprotein only, or with both G and F glycoprotein as described in Example 5. An additional control was a solution containing 6-CF diluted 1:20,000 only (no lipid control). Cells were replenished with 3 ml of a 1% DMEM cell culture medium and incubated at 37° C. in 5% $CO_2$. Cells were viewed after 1, 2, 4, and 24 hours under a fluorescent microscope at 40× magnification and photographed under phase and fluorescent light.

Cells incubated with diluted CF solution did not fluoresce. Cells incubated with artificial RSV envelopes without protein showed only faint occasional fluorescence. There was no detectable fluorescence from a field of cells incubated with lipid envelopes without protein (lipid control). Also, cells incubated with artificial RSV envelopes containing G glycoprotein or F glycoprotein only showed some, but relatively faint, fluorescence. However, practically all cells of a batch that had been incubated with the complete artificial RSV envelopes were fluorescent after 1 hour incubation. Fluorescence is in all cases diffuse within the cytoplasm of the cells, which confirms that the transfer process was a fusogenic process rather than a phagocytic process which would result in punctate fluorescence confined to intracellular vacuoles. These results indicate that the complete artificial RSV envelope is highly fusogenic and may therefore be used as a drug carrier to deliver drugs directly into the cytoplasm of infected cells.

We claim:

1. A two-step process for preparing lipid vesicles having a size of about 150 nm to about 300 nm and an approximately 1:1 cholesterol:phospholipid ratio characteristic of natural viruses and having antigenic or immunogenic proteins or peptides on the outer surface of said vesicle; said first step comprising solubilizing phospholipids and cholesterol in a sodium cholate detergent solution such that the molar ratio of detergent to total lipids is about 45:1, and the ratio of phospholipid to cholesterol is about 1:1, said first step further comprising the removal of said detergent by dialysis to obtain a rigid vesicle, said second step comprising insertion of proteins or peptides into the outer membrane of said vesicle, wherein the insertion of said proteins or peptides comprises mixing for about one hour said rigid vesicle from said first step with an aqueous solution of deoxycholate detergent, wherein the ratio of detergent to lipids is about 8:1, said process further comprising the addition of said proteins to said mixture of the deoxycholate detergent and the vesicle, followed by the removal of said detergent by dialysis.

2. The process, according to claim 1, wherein viral core proteins are incorporated into said lipid vesicle.

3. The process, according to claim 1, wherein said proteins or peptides are glycoproteins.

4. The process, according to claim 1, which further comprises a final step wherein said vesicles are freeze-dried.

5. The process, according to claim 3, wherein said glycoproteins are either natural or recombinant proteins from the human immune deficiency virus or the respiratory syncytial virus.

* * * * *

UNITED STATES PATENT AND TRADEMARK OFFICE
CERTIFICATE OF CORRECTION

PATENT NO.  : 5,252,348

DATED  : October 12, 1993

INVENTOR(S)  : Hans Schreier, Ramesh Chander, and Arlene A. Stecencko

It is certified that error appears in the above-identified patent and that said Letters Patent is hereby corrected as shown below:

Column 1  line 52: Delete "piposomes" and insert --liposomes--.

Column 2  line 34: Delete "process" and insert --processes--.

Column 10  line 62: Delete "deoxycholate detergent" and insert --deoxycholate (detergent--.

Signed and Sealed this

Sixth Day of February, 1996

*Attest:*

BRUCE LEHMAN

*Attesting Officer*  *Commissioner of Patents and Trademarks*